United States Patent
Celentano et al.

(10) Patent No.: US 8,894,262 B2
(45) Date of Patent: Nov. 25, 2014

(54) BLOOD GLUCOSE TEST STRIP ILLUMINATION DEVICE AND METHOD

(71) Applicant: Roche Diagnostics Operations, Inc., Indianapolis, IN (US)

(72) Inventors: Michael J. Celentano, Fishers, IN (US); Matthew C. Sauers, Indianapolis, IN (US); Anthony J. Uberta, III, Indianapolis, IN (US); Garrett S. Yesmunt, Indianapolis, IN (US)

(73) Assignee: Roche Diagnostic Operations, Inc., Indianapolis, IN (US)

( * ) Notice: Subject to any disclaimer, the term of this patent is extended or adjusted under 35 U.S.C. 154(b) by 99 days.

(21) Appl. No.: 13/793,406

(22) Filed: Mar. 11, 2013

(65) Prior Publication Data

US 2014/0254170 A1    Sep. 11, 2014

(51) Int. Cl.
*F21V 5/00* (2006.01)
*G02B 6/06* (2006.01)
*F21V 33/00* (2006.01)

(52) U.S. Cl.
CPC .................................. *F21V 33/0068* (2013.01)
USPC ..................... 362/572; 362/23.09; 362/23.16; 362/602

(58) Field of Classification Search
USPC .............................. 362/23.09, 23.16, 572, 602
See application file for complete search history.

(56) References Cited

U.S. PATENT DOCUMENTS

| 6,514,460 | B1 | 2/2003 | Fendrock |
| 7,154,592 | B2 * | 12/2006 | Reynolds et al. ............... 356/39 |
| 7,262,061 | B2 | 8/2007 | Petrich et al. |
| 2005/0009126 | A1 | 1/2005 | Andrews et al. |
| 2005/0265094 | A1 | 12/2005 | Harding et al. |
| 2005/0276133 | A1 | 12/2005 | Harding et al. |
| 2009/0227855 | A1 * | 9/2009 | Hill et al. ..................... 362/97.1 |
| 2010/0021342 | A1 | 1/2010 | Joseph et al. |
| 2012/0201048 | A1 * | 8/2012 | Prais ............................ 362/602 |

FOREIGN PATENT DOCUMENTS

| CN | 1146016 | 3/1997 |
| EP | 0407800 | 1/1991 |
| EP | 1199978 | 5/2002 |
| EP | 2377465 | 10/2011 |
| JP | 5164756 | 6/1993 |
| WO | WO2005/119234 | 12/2005 |
| WO | WO2012/006210 | 1/2012 |

* cited by examiner

*Primary Examiner* — Stephen F Husar

(74) *Attorney, Agent, or Firm* — Harness, Dickey & Pierce, P.L.C.

(57) ABSTRACT

A handheld test strip illumination device includes a housing. A strip connector positioned within the housing receives a first portion of a test strip in a test strip test position. A light source is positioned within the housing. A lens/light reflecting device is aligned to receive photons emitted from the light source and direct the photons onto the first portion of the test strip within the strip connector. The first portion of the test strip within the strip connector includes a longitudinal transparent layer receiving the photons emitted from the lens/light reflecting device within the housing. The photons pass through the longitudinal transparent layer and are emitted from the longitudinal transparent layer in a second portion of the test strip positioned outside of the housing, thereby illuminating a dose area of the test strip.

24 Claims, 5 Drawing Sheets

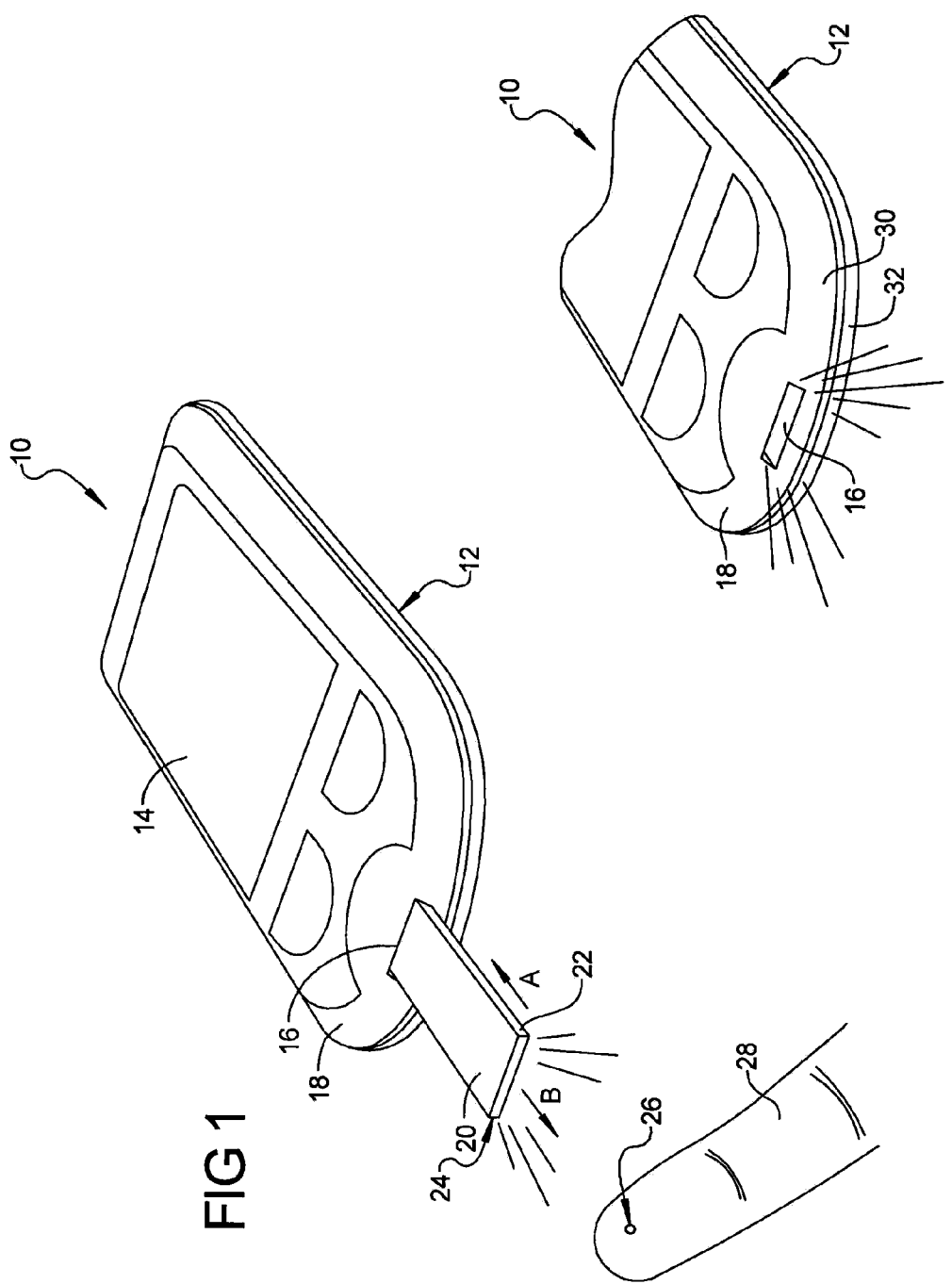

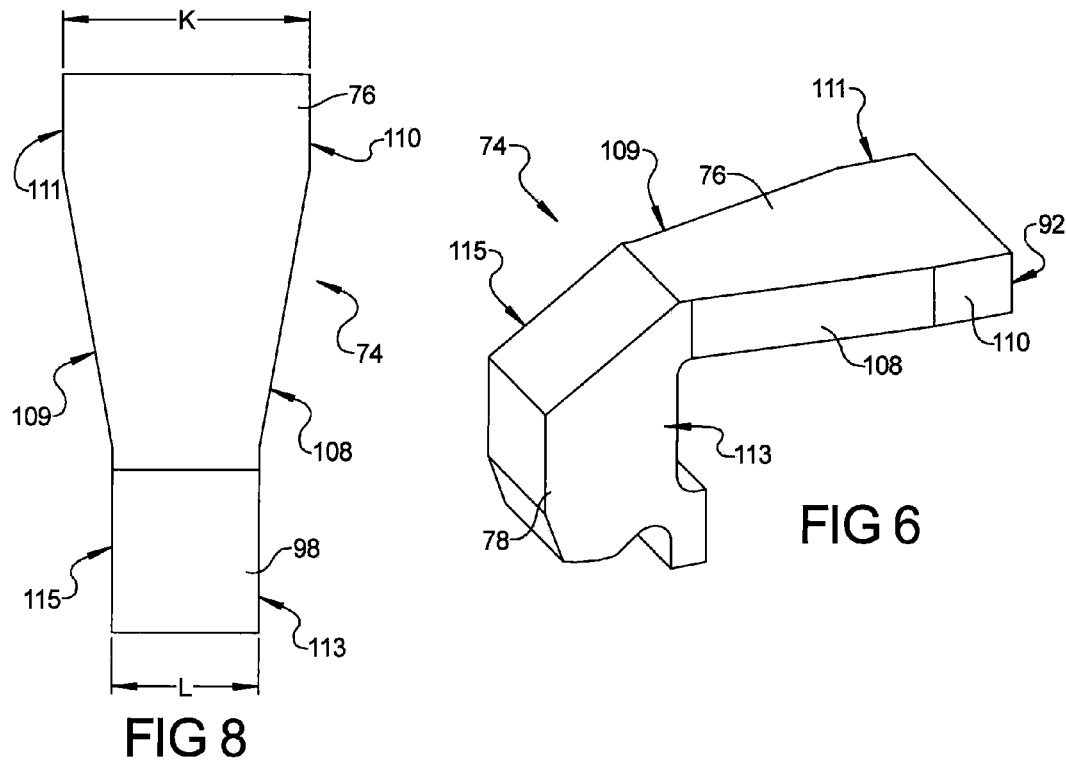
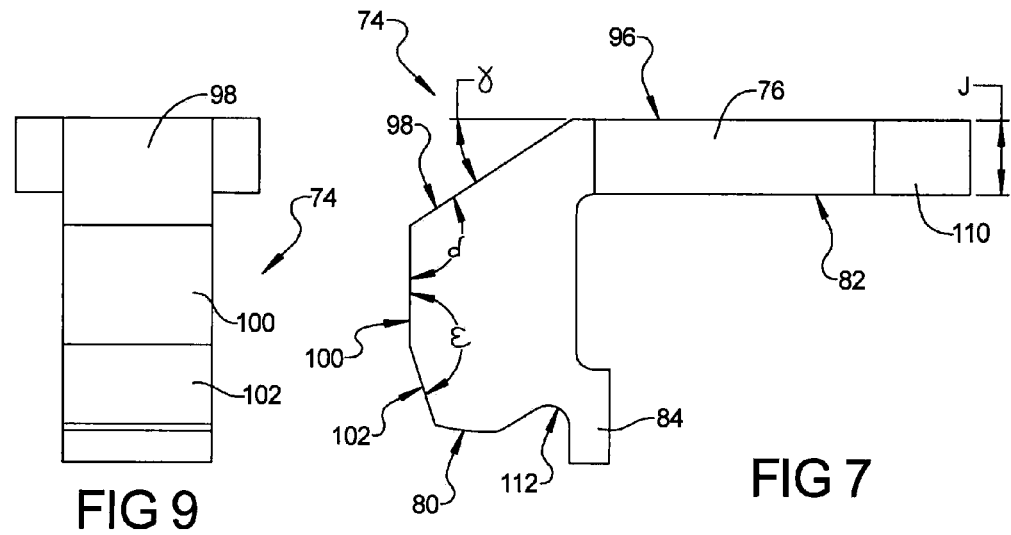

BLOOD GLUCOSE TEST STRIP ILLUMINATION DEVICE AND METHOD

FIELD

The present disclosure relates to a handheld diabetes managing device and, more particularly, relates to a handheld diabetes managing device with a light system for enhanced illumination of a test strip and an area proximate to the test strip.

BACKGROUND

Diabetes is managed primarily by controlling the level of glucose in the bloodstream. Management of diabetes is time-consuming for patients because of the need to consistently obtain reliable diagnostic information, follow prescribed therapy, and manage lifestyle on a daily basis. Diagnostic information, such as blood glucose, is typically obtained from a capillary blood sample with a lancing device and is then measured with a handheld blood glucose meter.

There are times in which the diabetes patient may wish to perform personal glucose testing in low light conditions. For instance, the patient may want to perform the test in a dark or poorly lit room. Because the test requires a certain amount of precision (e.g., proper placement of a blood droplet on the dosing area of a test strip), it can be difficult to complete the test in such conditions. Known handheld diabetes management devices providing illumination in such situations are not capable of providing all of the capabilities of illuminating the insertion location of a test strip, and where to deposit the blood sample or drop on the test strip.

SUMMARY

This section provides a general summary of the disclosure, and is not a comprehensive disclosure of its full scope or all of its features.

A handheld diabetes management device for providing enhanced illumination on a dosing area of a diabetes test element is disclosed. The diabetes management device includes a housing receiving a first portion of a test strip in a test position. A printed circuit board is positioned within the housing having an aperture. A light source is positioned within the housing. A lens/light reflecting device has a first light reflecting device portion and a second light reflecting device portion. The second light reflecting device portion extends through the aperture in the printed circuit board. The lens/light reflecting device is aligned to receive photons emitted from the light source and direct the photons onto the first portion of the test strip within the strip connector.

According to other aspects, a handheld test strip illumination device includes a housing. A strip connector positioned within the housing receives a first portion of a test strip in a test strip test position. A printed circuit board is positioned proximate to the strip connector within the housing, the printed circuit board having an aperture. A light source is positioned within the housing. A light reflecting device extends through the aperture in the printed circuit board. The light reflecting device is aligned to receive photons emitted from the light source and direct the photons onto the first portion of the test strip within the strip connector.

According to further aspects, a handheld test strip illumination device includes a housing. A strip connector positioned within the housing receives a first portion of a test strip in a test strip test position. A light source is positioned within the housing. A lens/light reflecting device is aligned to receive photons emitted from the light source and direct the photons onto the first portion of the test strip within the strip connector. The first portion of the test strip within the strip connector includes a longitudinal transparent layer receiving the photons emitted from the lens/light reflecting device within the housing. The photons pass through the longitudinal transparent layer to be emitted from the longitudinal transparent layer in a second portion of the test strip positioned outside of the housing.

According to other aspects, a handheld blood glucose test device providing enhanced illumination of a dosing area of a test strip includes a housing having a strip port receiving the test strip in a test strip test position. A strip connector positioned within the housing receives the test strip and has electrical contacts contacting individual test contacts of the test strip. A printed circuit board positioned within the housing has an aperture. A light emitting diode (LED) is connected to the printed circuit board. A lens/light reflecting device is supported on the printed circuit board and extends through the aperture in the printed circuit board into the strip connector. The lens/light reflecting device is aligned to receive light emitted from the LED and direct the light onto the test strip within the strip connector. The lens/light reflecting device has at least one reflective face redirecting the light received from the LED to a lens of the lens/light reflecting device. The lens focuses the light onto a transparent laminate of the test strip thereby illuminating a dosing area of the test strip positioned outside of the housing and the access port.

Moreover, a method of providing enhanced illumination on a dosing area of a diabetes test element of a handheld diabetes management device is disclosed. The method includes supporting the first light reflecting device portion of the lens/light reflecting device on the printed circuit board; extending the second light reflecting device portion of the lens/light reflecting device through the aperture in the printed circuit board into the strip connector; aligning the lens to direct the light onto a transparent laminate of the test strip; illuminating the light source; and directing the light using the lens into an end face of a longitudinal transparent layer of the test strip to illuminate a dosing area of the test strip.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

FIG. 1 is a perspective view of a handheld diabetes managing device according to the present teachings;

FIG. 2 is a perspective view of the handheld diabetes managing device of FIG. 1 depicting light exiting a strip port when a test strip is not present;

FIG. 6 is a left front perspective view of the lens/light reflecting device of FIG. 5;

FIG. 7 is a right side elevational view of a lens/light reflecting device of the device of FIG. 5;

FIG. 8 is a top plan view of the lens/light reflecting device of FIG. 5; and

FIG. 9 is a front elevational view of the lens/light reflecting device of FIG. 5.

Corresponding reference numerals indicate corresponding parts throughout the several views of the drawings.

DETAILED DESCRIPTION

Figure 3:
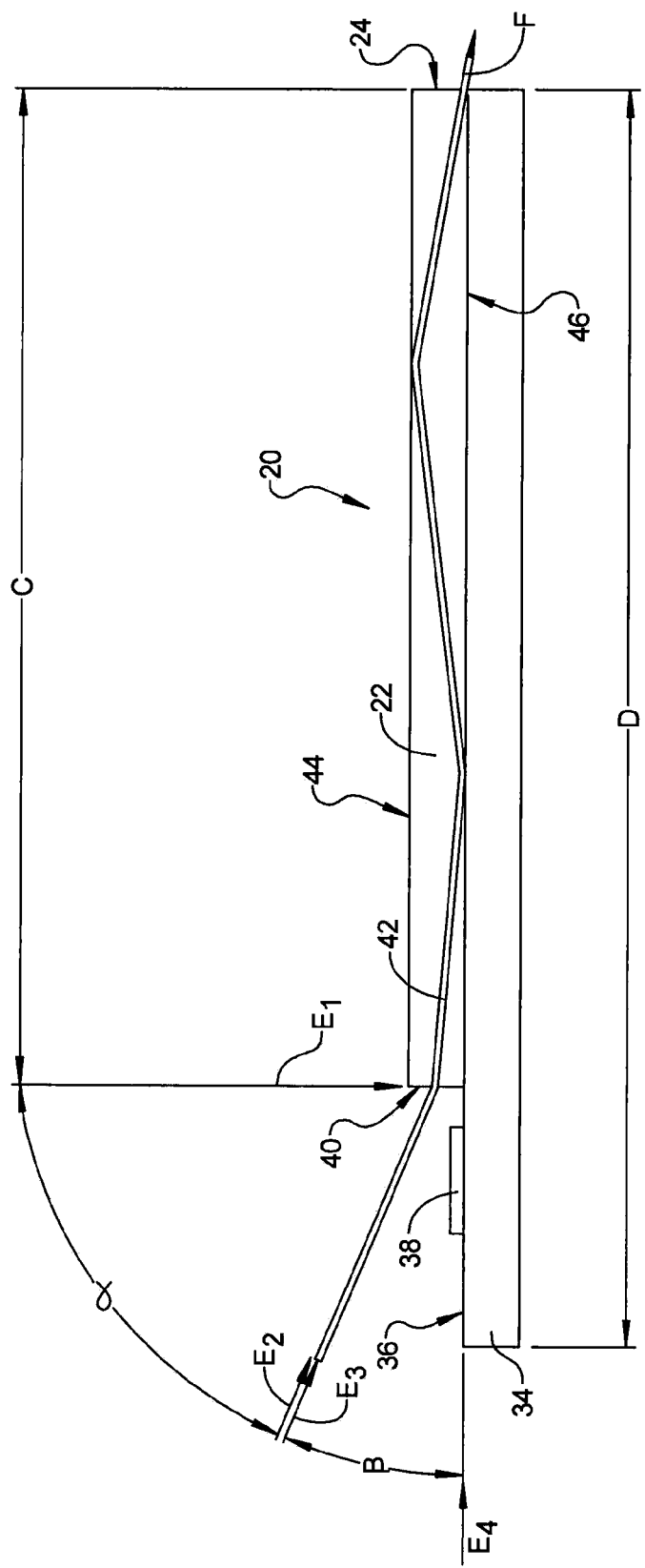
FIG. 3 is a side elevational view of a test strip of the present teachings.

Example embodiments will now be described more fully with reference to the accompanying drawings.

Referring initially to FIG. 1, an exemplary embodiment of a portable, handheld diabetes management device 10 is illustrated according to the present teachings. The diabetes management device 10 includes a housing 12 sized to fit in a hand of a user, and includes a view port or screen 14 which provides digital test results and provides for user input. A strip port 16 positioned at a body end 18 slidably receives a test strip 20 which includes at least one continuous, longitudinal transparent layer 22. Test strip 20 is slidably inserted in strip port 16 in an insertion direction "A" for testing, and is slidably removed in an opposite removal direction "B" at the conclusion of testing. Device 10 provides an internal light source which will be described in greater detail in reference to FIG. 4 which is capable of illuminating the longitudinal transparent layer 22 when test strip 20 is in the received test position shown. With the test strip 20 in a test position, light is emitted from a perimeter edge/dosing area 24 of the longitudinal transparent layer 22 such that a dose/sample 26 of a liquid from a user 28 such as the user's finger is illuminated, as well as the general area proximate to body end 18 of housing 12.

The device 10 can be used for analyzing a body fluid disposed on the perimeter edge/dosing area 24. For instance, as will be discussed, the test strip 20 can be a disposable glucose test strip. A droplet of blood can be applied from dose/sample 26 while the test strip 20 is inserted within the device 10, and the device 10 can analyze the droplet to detect a blood glucose level therein. It will be appreciated, however, that the device 10 could be used for analyzing any other suitable characteristic of any other body fluid without departing from the scope of the present disclosure.

Referring to FIG. 2, the device 10 can include first and second portions 30, 32 of housing 12. The first and second portions 30, 32 can be removably coupled together such that the first and second portions 30, 32 define an interior space there-between, which is used to house various components therein, as will be discussed below. When the test strip 20 is not positioned in the strip port 16, light generated from within housing 12 is emitted through strip port 16 to illuminate the area about body end 18 as discussed above, which also is effective in low light areas to assist the user in aligning the test strip 20 and/or to improve visibility of the area at dose/sample 26. In some aspects, the strip port 16 can be a through hole with an ovate or rectangular shape extending through body end 18 of the first portion 30 of the housing 12. In other aspects, the strip port 16 can be a through hole with an ovate or rectangular shape extending through the second portion 32.

Referring now to FIGS. 3 and 1-2, the test strip 20 is created as a multiple layer strip having at least longitudinal transparent layer 22 defining a first layer which is applied onto a second layer 34. Longitudinal transparent layer 22 has a length "C" which is less than a length "D" of the second layer 34, such that a free surface 36 having electrical contacts 38 extends beyond an end face 40 of the longitudinal transparent layer 22. According to several aspects, the longitudinal transparent layer 22 of test strip 20 is used as a photonic travel path for light generated within the device 10 to be directed out of device 10. For this use, photons cannot create a light transmission path 42 if an incident ray "E" is oriented within a range of incident rays "$E_1$" to "$E_2$" defining an angular range alpha ($\alpha$), which according to several aspects is from zero degrees or normal to longitudinal transparent layer 22 to approximately 44 degrees. Photons will create the light transmission path 42 if the incident ray "E" is oriented within a range of incident rays "$E_3$" to "$E_4$" defining an angular range beta ($\beta$), which according to several aspects ranges from approximately 45 degrees to approximately 90 degrees measured with respect to incident ray "$E_1$". Light transmission path 42 will be successfully created between end face 40 and perimeter edge/dosing area 24 of the longitudinal transparent layer 22 within angular range $\beta$ which can include reflection off an upper surface 44 and a lower surface 46 of longitudinal transparent layer 22. The photons will exit as emitted light rays "F" as shown and described in reference to FIG. 1 and/or FIG. 2.

Referring to FIG. 4 and again to FIGS. 1-3, various internal components that are contained within the housing 12 create a testing mechanism 48. For instance, testing mechanism 48 can include a circuit board 50 which supports a strip connector 52. The circuit board 50 can be a printed circuit board with various circuits and circuit components included thereon. According to several aspects, a hole or aperture 54 is created through circuit board 50 which separates circuit board 50 into a first circuit board portion 56 and a second circuit board portion 58. A strip connector aperture 59 separates strip connector 52 into a first strip connector portion 60 and a second strip connector portion 62. Strip connector 52 provides a strip receiving channel 64 which slidably receives a free end 66 of the second layer 34 of test strip 20 such that electrical conductors 68 created on test strip 20 directly engage the electrical contacts 38 when test strip 20 is in the test position shown. Free end 66 and the portion of longitudinal transparent layer 22 positioned within housing 12 in the test strip test position define a first test strip portion 67. The portions of longitudinal transparent layer 22 and second layer 34 of test strip 20 that extend outward of housing 12 in the test strip test position define a second test strip portion 69. Test strip 20 is supported in the test position by a planar surface 70 of a beam 72.

Figure 4:
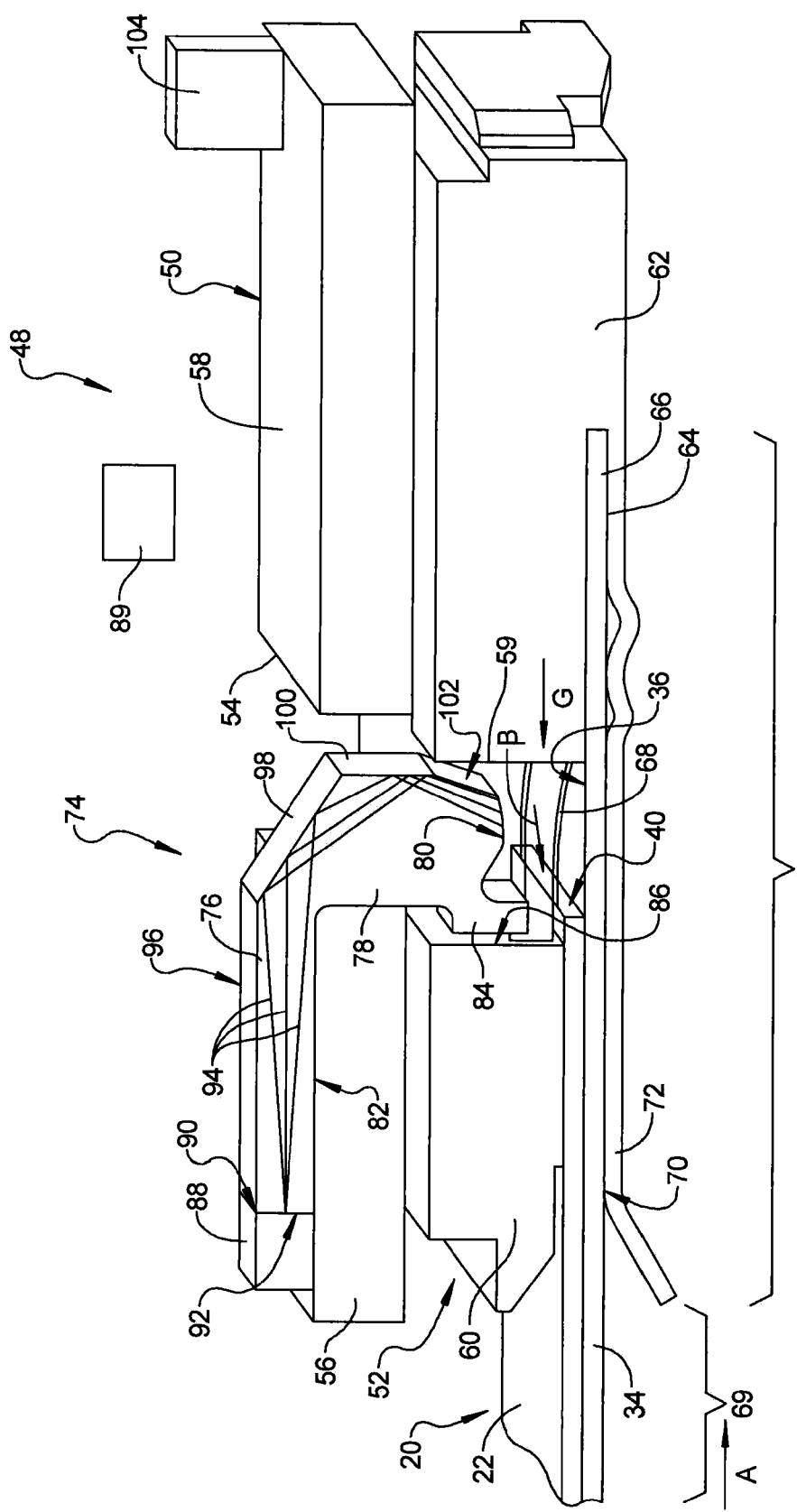
FIG. 4 is a side elevational perspective view of the interior components of the handheld diabetes managing device of FIG. 1.

With continuing reference to FIG. 4 and as previously described in reference to FIG. 3, it is desirable to have photons enter at end face 40 for transfer through longitudinal transparent layer 22 such that the photons are emitted from the longitudinal transparent layer 22 at the second test strip portion 69 which extends outwardly from housing 12. The emitted photons also act to illuminate the second test strip portion 69. It is evident that a photon incidence path "G" colinear with respect to longitudinal transparent layer 22 provides an optimal photon incidence path, however, the configuration of second strip connector portion 62 precludes positioning a light source at a position to generate incidence path "G". A functional path of photon incidence is therefore provided by use of a lens/light reflecting device 74. Lens/light reflecting device 74 is made of a light transmissive or transparent material such as an injection molded polymeric material which can include a polycarbonate resin thermoplastic. In order to redirect the photons, the lens/light reflecting device 74 includes a first light reflecting device portion 76 supported on first circuit board portion 56 and a second light reflecting device portion 78 which extends through the aperture 54. According to further aspects, the strip connector aperture 59 is aligned with the aperture 54 of the printed circuit board 50, therefore the second light reflecting device portion 78 also extends through both the aperture 54 in the printed circuit board 50 and the strip connector aperture 59. Second light reflecting device portion 78 provides an integral lens 80 from which photons are emitted within the angular range β (described in reference to FIG. 3) for optimum entrance to end face 40 and subsequent transfer through longitudinal transparent layer 22. According to several aspects, the first light reflecting device portion 76 includes a first planar surface 82 which can directly abut with and therefore support the first light reflecting device portion 76 on the first circuit board portion 56. According to other aspects, the second light reflecting device portion 78 can include an extending arm 84 which can directly abut with and therefore connect the second light reflecting device portion 78 to an inner wall 86 of the first strip connector portion 60 within the aperture 54. The extending arm 84 is spatially separated from the lens 80.

According to several aspects, end face 40 is oriented normal to second layer 34, therefore determining the angular range β described in reference to FIG. 3. In other aspects, end face 40 can be oriented at an angle less than or more than 90 degrees with respect to second layer 34, which will increase or decrease the angular range β within which photons enter end face 40 for transfer through longitudinal transparent layer 22. A geometry (e.g., the curvature) of lens 80 is and the angles of the reflective faces are modified in these aspects to ensure light photons are directed at end face 40 to achieve light travel through longitudinal transparent layer 22.

A light source 88 is provided within housing 12 that can be mounted to the circuit board 50, and according to several aspects is mounted to first circuit board portion 56. The light source 88 can be of any suitable type for photon generation, such as a light emitting diode (LED). The circuit board 50, a control processor 89 for controlling the operation of device 10, and the light source 88 can each be housed within housing 12. Because a direct path for light from light source 88 aimed directly at the end face 40 of test strip 20 to suit the requirements of angular range beta (β) may not be available, light source 88 is oriented to position a light emitting face 90 of light source 88 in direct alignment with, and according to several aspects in direct contact with a light reflecting device end face 92 of first light reflecting device portion 76 of lens/light reflecting device 74. Various photon paths 94 can be redirected by use of multiple reflective faces of lens/light reflecting device 74. These can include but are not limited to a second planar surface 96 which is parallel with but oppositely facing with respect to first planar surface 82 of first light reflecting portion 76, a first reflective face 98, a second reflective face 100, and a third reflective face 102. Each of the first and second planar surfaces 82, 96 and the first, second and third reflective faces 98, 100, 102 reflect and direct light photons from light source 88 through lens 80. According to several aspects lens 80 defines a convex, compound curve acting to direct photons into the angular range β.

The device 10 can additionally include a measurement engine 104. The measurement engine 104 can be of a known type for analyzing the body fluid applied to the test strip 20 as discussed above. The measurement engine 104 can be operably mounted to the circuit board 50 and/or strip connector 52. As such, when the test strip 20 is inserted within the strip port 16 and the body fluid is applied, the measurement engine 104 can perform the predetermined analysis. Moreover, the measurement engine 104 can include associated software and logic (e.g., within the control processor 89) for performing and controlling the analysis of the body fluid.

As shown in FIGS. 1, 2 and 4, the device 10 can include display 14. The display 14 can be operably connected to the control processor 89 for displaying various information (e.g., text, graphics, icons, and other objects) relating to the operation of the device 10. According to several aspects, the display 14 is operably supported by the first portion 30 of the housing 12, however, display 14 can also be supported by the second portion 32. The display 14 can provide digital switches/icons which permit the user to select from different test functions, and/or to slidably remove the test strip 20 at the conclusion of the testing phase.

Figure 5:
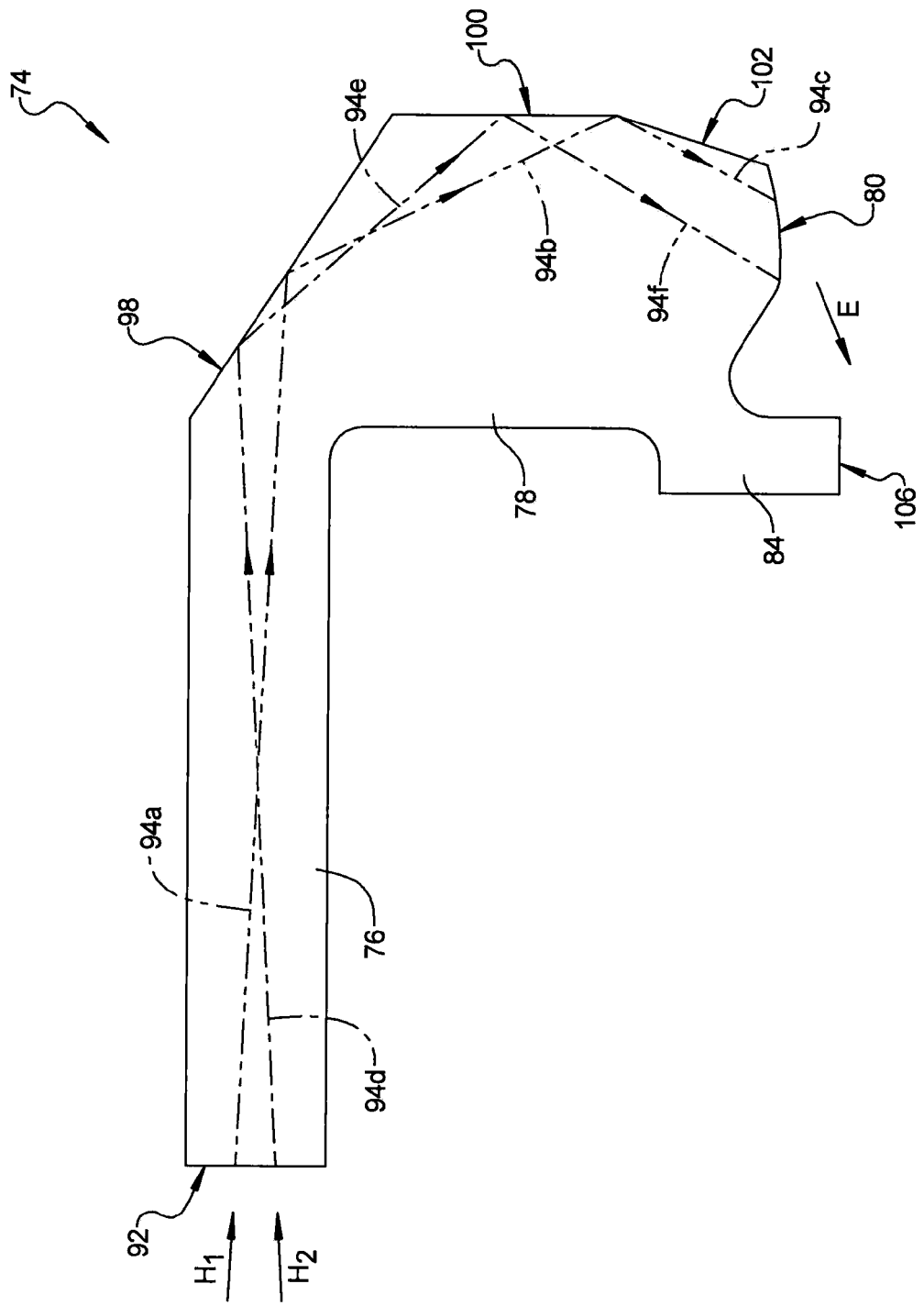
FIG. 5 is a left side elevational view of a lens/light reflecting device of the device of FIG. 1.

As shown in FIG. 5 and referring again to FIG. 3, a first exemplary photon ray path 94a,b,c through lens/light reflecting device 74 is shown. Upon entering the light reflecting device end face 92 in a path "$H_1$", a first path portion 94a is reflected off first reflective face 98 and directed toward either second or third reflective face 100, 102. In the first example shown, a second path portion 94b is directed to the third reflective face 102 where it is reflected as a third path portion 94c to the lens 80. A second exemplary photon ray path 94d,e,f through lens/light reflecting device 74 is also shown. Upon entering the light reflecting device end face 92 in a path "$H_2$", a first path portion 94d is reflected off first reflective face 98 and directed in a second path portion 94e to the second reflective face 100 where it is reflected as a third path portion 94f to the lens 80. Lens 80 is adapted such that any ray path 94 "H" that enters light reflecting device end face 92 and strikes any portion of lens 80 will be focused within the angular range β. An end face 106 of extending arm 84 is positioned to prevent any portion of extending arm 84 from interfering with incident ray "E". The lengths of first and second light reflecting device portions 76, 78 and the refractive index of the material of lens/light reflecting device 74 are selected to provide a focal length required to achieve light emission via lens 80 within the angular range β.

As shown in FIGS. 6-9, according to several aspects the lens/light reflecting device 74 can have the first light reflecting device portion 76 and the second light reflecting device portion 78 integrally connected so as to be monolithic, and can be created using a molding process such as injection molding. It will be appreciated that the first and second light reflecting device portions 76, 78 of the lens/light reflecting device 74 can have any other suitable shape. For instance, the first light reflecting device portion 76 can have one or more rounded (convex or concave) outer surfaces. Moreover, the second light reflecting device portion 78 can have any number of flat reflective surfaces. Furthermore, lens 80 can also have a concave, or a combination of a convex/concave curvature in addition to the convex curvature depicted. The lens/light reflecting device 74 can be made out of or include a light transmissive material. For instance, the lens/light reflecting device 74 can be made out of or include a rigid, polymeric, light transmissive material. In other embodiments, the lens/light reflecting device 74 can be made out of or include a flexible, light transmissive material, allowing the light source 88 to be positioned anywhere within the device.

According to several aspects first light reflecting device portion 76 includes a tapering body having angular first and second side walls 108, 109 that individually meet third and fourth side walls 110, 111 proximate to light reflecting device end face 92. Third and fourth side walls 110, 111 are oriented parallel with respect to each other. A maximum width "K" of lens/light reflecting device 74 is provided between third and fourth side walls 110, 111 and therefore proximate to light reflecting device end face 92. A concave curved surface 112 separates the extending arm 84 from lens 80. The second light reflecting device portion 78 has opposed parallel side walls 113, 115 that are oriented parallel to third and fourth side walls 110, 111, and define a second light reflecting device portion width "L", which is less than maximum width "K".

As best seen in reference to FIG. 7, the first reflective face 98 is oriented at an acute angle gamma (γ) with respect to second planar surface 96. According to several aspects, second reflective face 100 is oriented normal to second planar surface 96. An obtuse angle angle delta (δ) is defined between first reflective face 98 and second reflective face 100. According to several aspects, third reflective face 102 is oriented at an obtuse angle epsilon (ε) with respect to second reflective face 100. In one exemplary embodiment of lens/light reflecting device 74 using a polycarbonate material, angle gamma (γ) is approximately 34 degrees, angle delta (δ) is approximately 124 degrees, and angle epsilon (ε) is approximately 163 degrees.

The lens/light reflecting device 74 can be coupled to the circuit board 50 as shown in FIG. 4. As shown in FIG. 4, the aperture 54 can be shaped and sized so as to define a clear opening that closely matches the outer periphery of the second light reflecting device portion 78 of lens/light reflecting device 74. In some embodiments, the lens/light reflecting device 74 can be retained by friction, by an interference fit, by adhesives, by a fastener, or in any other manner.

Also as shown in FIGS. 1 and 4, the lens/light reflecting device 74 aligns light photons to pass through the longitudinal transparent layer 22 of test strip 20 to illuminate the dosing area 24 of the test strip 20 external to device 10. The light transmitted from the lens/light reflecting device 74 and longitudinal transparent layer 22 can thereby illuminate the dosing area 24. As such, the user can more easily recognize where to apply a blood droplet for glucose analysis, and proper application of the blood droplet to the dosing area 24 is more likely. Further, as shown in FIGS. 2 and 4, prior to insertion of test strip 20 or when test strip 20 is absent, device 10 can be operated such that the lens/light reflecting device 74 aligns light photons to pass outward through the strip port 16 to illuminate the area of dose/sample 26 external to device 10. It is also anticipated that a portion of the light emitted by light source 88 and exiting lens 80 will be emitted through strip port 16 about a perimeter of test strip 20 when test strip 20 is in the test position.

It will also be appreciated that the device 10 can provide enhanced illumination efficiently and cost effectively. The lens/light reflecting device 74 can be relatively inexpensive. The circuit board 50 can be manufactured independently with the light source 88 included thereon before being assembled within the housing 12. Then, during assembly of the device 10, the circuit board 50 having light source 88 can be positioned within housing 12, such that the lens/light reflecting device 74 is in its proper position for receiving light from the light source 88. The lens/light reflecting device 74 is then ready for transmitting light out of the housing 12 through the longitudinal transparent layer 22 of test strip 20.

The lens/light reflecting device 74 described herein is a light reflecting device used to redirect light photons from light source 88 to the end face 40 of test strip 20 by the use of its refractory index and the various reflective faces. According to other aspects, the functions of lens/light reflecting device 74 can be more broadly provided in a light reflecting device having one or more reflective faces, mirrors, or the like that are oriented to reflect light from light source 88 to end face 40 of the test strip 20.

Thus, the lens/light reflecting device 74 and associated components of the device 10 directing light through the longitudinal transparent layer 22 of test strip 20 can assist the user in performing analyses, especially in low ambient light conditions. Furthermore, the device 10 can provide various types of feedback to further assist the user. The light source 88 can be actuated in multiple ways. These include but are not limited to a user actuated switch or icon that actuates light source 88, the light source being automatically actuated by insertion of the test strip 20, and/or the light source 88 being actuated when device 10 is actuated. Light source 88 can be actuated for an entire time of operation of device 10, only during a testing phase, or for a time period selected by the user or by user actuation.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A handheld test strip illumination device, comprising:
    a housing having a strip connector within the housing receiving a first portion of a test strip in a test position;
    a printed circuit board positioned within the housing and having an aperture;
    a light source positioned within the housing; and
    a lens/light reflecting device having a first light reflecting device portion and a second light reflecting device portion, the second light reflecting device portion extending through the aperture in the printed circuit board, the lens/light reflecting device aligned to receive photons emitted from the light source and direct the photons onto the first portion of the test strip within the strip connector.

2. The handheld test strip illumination device of claim 1, further including a strip connector positioned within the housing receiving the first portion of the test strip in the test position, wherein the first portion of the test strip within the strip connector includes a longitudinal transparent layer, the longitudinal transparent layer including an end face receiving the photons emitted from the light source at an angle of incidence allowing the photons to pass entirely through the longitudinal transparent layer to be emitted from the longitudinal transparent layer in a second portion of the test strip positioned outside of the housing.

3. The handheld test strip illumination device of claim 2, wherein the angle of incidence is within an angular range greater than or equal to approximately 45 degrees and less than or equal to 90 degrees determined with respect to a direction normal to the longitudinal transparent layer.

4. The handheld test strip illumination device of claim 2, wherein the strip connector includes a strip connector aperture aligned with the aperture of the printed circuit board, the second light reflecting device portion extending through both the aperture in the printed circuit board and the strip connector aperture.

5. The handheld test strip illumination device of claim 1, wherein the second light reflecting device portion of the lens/light reflecting device includes a curved lens acting to direct the photons into an angular range greater than or equal to approximately 45 degrees determined with respect to a direction normal to a longitudinal transparent layer of the test strip, the curved lens defining a convex curve facing the test strip.

6. The handheld test strip illumination device of claim 1, wherein the lens/light reflecting device includes a lens and first, second and third reflective faces, the first, second and third reflective faces individually acting to direct the photons emitted by the light source through the lens at the first portion of the test strip.

7. The handheld test strip illumination device of claim 6, wherein the first light reflecting device portion of the lens/light reflecting device includes opposed, planar first and second surfaces reflecting the photons toward one of the first, second or third reflective faces.

8. The handheld test strip illumination device of claim 1, wherein the light source is connected to a first circuit board portion of the printed circuit board proximate to the first light reflecting device portion.

9. The handheld test strip illumination device of claim 1, wherein:
    the first light reflecting device portion is partially supported on a first circuit board portion of the printed circuit board; and
    the lens/light reflecting device further includes an extending arm directly abutting an inner wall of the first strip connector portion within the aperture.

10. A handheld test strip illumination device, comprising:
    a housing;
    a strip connector positioned within the housing receiving a first portion of a test strip in a test strip test position;
    a printed circuit board positioned proximate to the strip connector within the housing, the printed circuit board having an aperture;
    a light source positioned within the housing; and
    a light reflecting device extending through the aperture in the printed circuit board, the light reflecting device aligned to receive photons emitted from the light source and direct the photons onto the first portion of the test strip within the strip connector.

11. The handheld test strip illumination device of claim 10, wherein the light reflecting device comprises a lens/light reflecting device having a first light reflecting device portion and a second light reflecting device portion defining a monolithic device, the second light reflecting device portion extending through the aperture in the printed circuit board.

12. The handheld test strip illumination device of claim 11, wherein the first light reflecting device portion is supported on the printed circuit board.

13. The handheld test strip illumination device of claim 10, wherein the first portion of the test strip within the strip connector includes:
    a longitudinal transparent layer receiving the photons emitted from the light source within the housing, the photons passing through the longitudinal transparent layer to be emitted from the longitudinal transparent layer in a second portion of the test strip positioned outside of the housing; and
    an end face receiving the photons emitted from the light source at an angle of incidence allowing the photons to pass through the longitudinal transparent layer.

14. The handheld test strip illumination device of claim 13, wherein the housing includes a strip port slidably receiving the test strip, the photons being also emitted from within the housing outward through the strip port, the photons thereby illuminating an area proximate to the strip port outside of the housing.

15. The handheld test strip illumination device of claim 11, wherein the strip connector includes a strip connector aperture aligned with the aperture of the printed circuit board such that the light reflecting device extends through both the aperture in the printed circuit board and the strip connector aperture.

16. A handheld test strip illumination device, comprising:
    a housing;
    a strip connector positioned within the housing receiving a first portion of a test strip in a test strip test position;
    a light source positioned within the housing;
    a lens/light reflecting device aligned to receive photons emitted from the light source and direct the photons onto the first portion of the test strip within the strip connector; and the first portion of the test strip within the strip connector including a longitudinal transparent layer receiving the photons emitted from the lens/light reflecting device within the housing, the photons passing through the longitudinal transparent layer to be emitted from the longitudinal transparent layer in a second portion of the test strip positioned outside of the housing.

17. The handheld test strip illumination device of claim 16, further including a printed circuit board positioned proximate to the strip connector within the housing, the printed circuit board having an aperture, the lens/light reflecting device extending through the aperture in the printed circuit board.

18. The handheld test strip illumination device of claim 17, wherein the lens/light reflecting device includes a first light reflecting device portion and a second light reflecting device portion, the second light reflecting device portion extending through the aperture in the printed circuit board.

19. The handheld test strip illumination device of claim 18, wherein the strip connector includes a strip connector aperture aligned with the aperture of the printed circuit board, the second light reflecting device portion extending through both the aperture in the printed circuit board and the strip connector aperture.

20. The handheld test strip illumination device of claim 17, wherein the strip connector includes a strip connector aperture aligned with the aperture of the printed circuit board, the lens/light reflecting device further extending through the strip connector aperture.

21. The handheld test strip illumination device of claim 16, wherein:
the lens/light reflecting device includes a lens and at least first and second reflective faces, the first and second reflective faces individually acting to direct the photons emitted by the light source through the lens at the first portion of the test strip; and
the first light reflecting device portion of the lens/light reflecting device includes opposed, planar first and second surfaces reflecting the photons toward one of the first and second reflective faces.

22. The handheld test strip illumination device of claim 16, wherein:
the lens/light reflecting device includes a lens and first, second and third reflective faces, the first, second and third reflective faces individually acting to direct the photons emitted by the light source through the lens at the first portion of the test strip; and
the first light reflecting device portion of the lens/light reflecting device includes opposed, planar first and second surfaces reflecting the photons toward one of the first, second or third reflective faces.

23. The handheld test strip illumination device of claim 16, wherein:
the longitudinal transparent layer includes an end face receiving the photons emitted from the light source at an angle of incidence allowing the photons to pass through the longitudinal transparent layer;
the lens/light reflecting device includes a lens, the lens acting to direct the photons toward the end face in the test strip test position; and
the lens defines a convex compound curve shape.

24. The handheld test strip illumination device of claim 16, wherein the second portion of the test strip positioned outside of the housing is illuminated by the photons passing through the longitudinal transparent layer.

* * * * *